United States Patent
Koester

(10) Patent No.: US 9,791,354 B2
(45) Date of Patent: Oct. 17, 2017

(54) INLINE PRE-FILTER FOR ASPIRATED DETECTORS

(71) Applicant: Honeywell International Inc., Morristown, NJ (US)

(72) Inventor: Ludger Koester, Aurora, IL (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 215 days.

(21) Appl. No.: 14/605,411

(22) Filed: Jan. 26, 2015

(65) Prior Publication Data

US 2016/0214048 A1  Jul. 28, 2016

(51) Int. Cl.
| | |
|---|---|
| *G01N 1/22* | (2006.01) |
| *B01D 46/42* | (2006.01) |
| *G08B 17/10* | (2006.01) |
| *B01D 46/00* | (2006.01) |
| *G08B 17/00* | (2006.01) |

(52) U.S. Cl.
CPC ......... *G01N 1/2205* (2013.01); *B01D 46/009* (2013.01); *B01D 46/4272* (2013.01); *G08B 17/10* (2013.01); *B01D 46/0005* (2013.01); *B01D 46/0097* (2013.01); *B01D 2201/0461* (2013.01); *B01D 2201/30* (2013.01); *B01D 2201/302* (2013.01); *B01D 2201/307* (2013.01); *G08B 17/00* (2013.01)

(58) Field of Classification Search
CPC .............. B01D 46/0097; B01D 46/005; B01D 46/4272; B01D 2201/0461; B01D 2201/30; B01D 2201/302; B01D 2201/307; G01N 1/2205; G08B 17/00
USPC ....................................................... 73/28.04
See application file for complete search history.

(56) References Cited

U.S. PATENT DOCUMENTS

| | | | |
|---|---|---|---|
| 3,327,858 A | 6/1967 | Eddy et al. | |
| 4,682,993 A * | 7/1987 | Todd .................. | B01D 46/0002 210/235 |
| 4,721,563 A | 1/1988 | Rosaen | |
| 5,610,592 A | 3/1997 | Okazaki | |
| 5,846,417 A * | 12/1998 | Jiang ..................... | B01D 29/15 210/235 |
| 6,171,491 B1 * | 1/2001 | Popoff .................. | B01D 27/07 210/235 |
| 2010/0271219 A1 | 10/2010 | Lang | |
| 2015/0022363 A1 | 1/2015 | Lang et al. | |
| 2016/0223437 A1 * | 8/2016 | Ajay ...................... | G01N 15/06 |

FOREIGN PATENT DOCUMENTS

WO   WO 2008/061317 A1   5/2008

OTHER PUBLICATIONS

Partial European search report from corresponding EP patent application16151969.9, dated Jun. 7, 2016.
Extended European search report from corresponding EP patent application 16151969.9, dated Oct. 14, 2016.

* cited by examiner

*Primary Examiner* — Peter Macchiarolo
*Assistant Examiner* — Timothy Graves
(74) *Attorney, Agent, or Firm* — Husch Blackwell LLP

(57) ABSTRACT

An apparatus which includes an aspirated smoke detector, and a pre-filter coupled to an inflow port of the detector wherein the pre-filter carries a removable filter element. The filter element is configured such that when it is removed, fluid flow through the filter is blocked. When the filter element is present in the pre-filter, fluid flow through the filter is permitted.

13 Claims, 4 Drawing Sheets

INLINE PRE-FILTER FOR ASPIRATED DETECTORS

FIELD

The application pertains to aspirated smoke detectors. More particularly, the application pertains to such smoke detectors which include a pre-filter attached to an inflow port of the detector to prevent pollution from entering a sensing chamber of the detector.

BACKGROUND

Aspirated smoke detectors draw air from a variety of locations via a fan thru a piping system into a common detection chamber. The piping system has several holes in different locations thru which smoke/air will be drawn to the smoke detector.

Representative detectors are disclosed in published U.S. patent applications such as 2010/0271219 published Oct. 28, 2010, entitled "Variable Air Speed Aspirating Smoke Detector", and 2015/0022363 published Jan. 22, 2015, entitled, "Multi-Channel Aspirated Smoke Detector". The '219 and '363 applications are assigned to the assignee hereof and are incorporated herein by reference.

Aspirated smoke detectors are often used in industrial settings such as coal mines or flour mills. In such environments there can be extensive airborne pollution in the form of airborne particulate matter. Such detectors need to be protected against air pollution.

Known detectors often include a built-in filter. But there are many applications where the air is so polluted that a pre-filter with an easy changeable filter medium needs to be installed. There are some pre-filters on the market for use with aspirated detectors. However, if the filter medium is missing because it was taken out, for example because of being dirty, and in need of replacement, and if not promptly replaced then polluted air can flow into the detector and the sensing chamber.

There is a need to address the deficiencies of known pre-filters.

DETAILED DESCRIPTION

Figure 1:
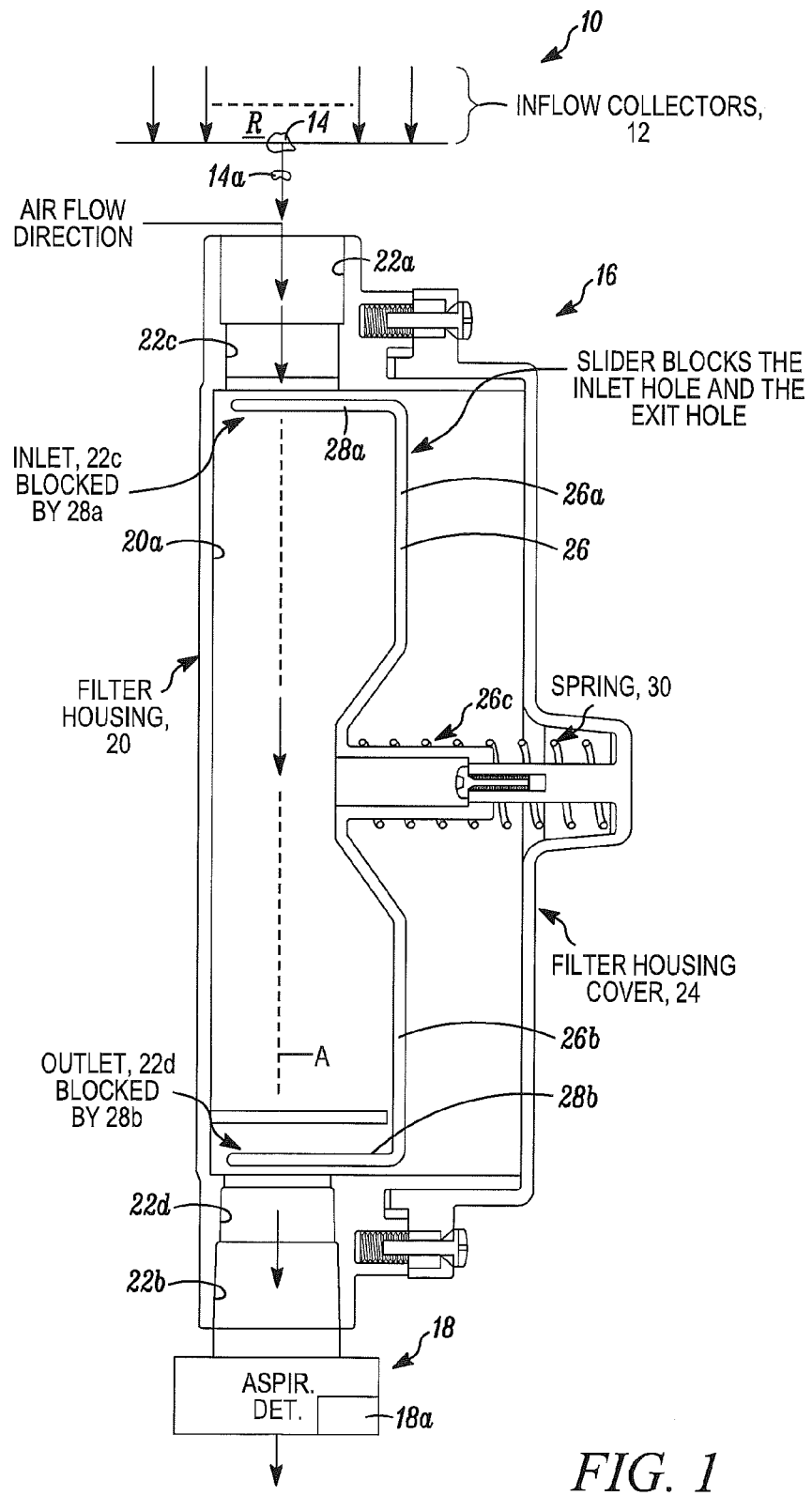
FIG. 1 is a diagram of a system in accordance herewith, the pre-filter is illustrated in a side sectional view.

While disclosed embodiments can take many different forms, specific embodiments hereof are shown in the drawings and will be described herein in detail with the understanding that the present disclosure is to be considered as an exemplification of the principles hereof, as well as the best mode of practicing same, and is not intended to limit the claims hereof to the specific embodiment illustrated.

As explained below, in one aspect, a pre-filter in accordance herewith will block the air flow and give the aspiration detector a warning. Almost all known aspiration detectors measure the velocity of the air coming into the aspiration unit. If there is a large variation in velocity, for example +/−20% than the unit will alarm.

In another aspect, a pre-filter in accordance herewith will block the fluid or smoke inflow pipe, if the filter medium is missing. In response to this blockage, the aspiration detector will alarm. That will prevent the aspiration detector from drawing air into the sensing chamber. This will protect the detector against a sudden inflow of pollution.

In a disclosed embodiment, the filter includes a housing, a cover, a filter medium, a right-angle-slider and a biasing element such as a spring. The housing has a fluid or air inflow port or opening, and a fluid or air outflow port or opening.

If the filter medium is installed it will push the right-angle-slider away from one or both of the inflow port or the outflow port. and air can flow thru the filter. However, if the filter medium is not installed then the spring will push the right-angle-slider over one or both of the inflow port or outflow port and prevent the polluted air from flowing into the sensing chamber of the aspiration detector. In this condition, flow into the sensing chamber drops suddenly, almost to no flow. The aspiration detector will then alarm because of low internal fluid, or, air velocity.

The force of the spring is so designed so that the filter medium can compress it. The right-angle-slider could also be installed that it will block the exit port, opening. Either alternate comes within the spirit and scope hereof. In yet another embodiment, the spring can be installed in the housing instead of the cover.

FIG. 1 illustrates a system 10 in accordance herewith. In system 10, a plurality of inflow collectors, or perforated pipes, 12 provide flow paths from a plurality of locations in a region R being monitored to a manifold 14 which combines them into a single inflow path 14a. Ambient air in the region R is drawn through collection pipes 12, into single pipe 14a to a pre-filter 16.

Incoming atmospheric samples flow through pre-filter 16 and into and through aspirated detector 18. Detector 18 as will be understood by those of skill in the art can include an aspiration unit, a fan or blower, along with control circuits 18a which can provide indicators of various conditions.

Pre-filter 16 can include a housing 20 which defines an internal region 20a. Housing 20 carries a fluid or air flow input port 22a and an outflow port 22b. Incoming fluid samples, from inflow port 22a, if not blocked by pre-filter 16, flow through inlet 22c, through the internal region 20a along axis A through outlet 22d, and the out the outflow port 22b and into the aspiration detector 18. A cover 24 is carried on housing 20 and closes internal region 20a.

Figure 2:
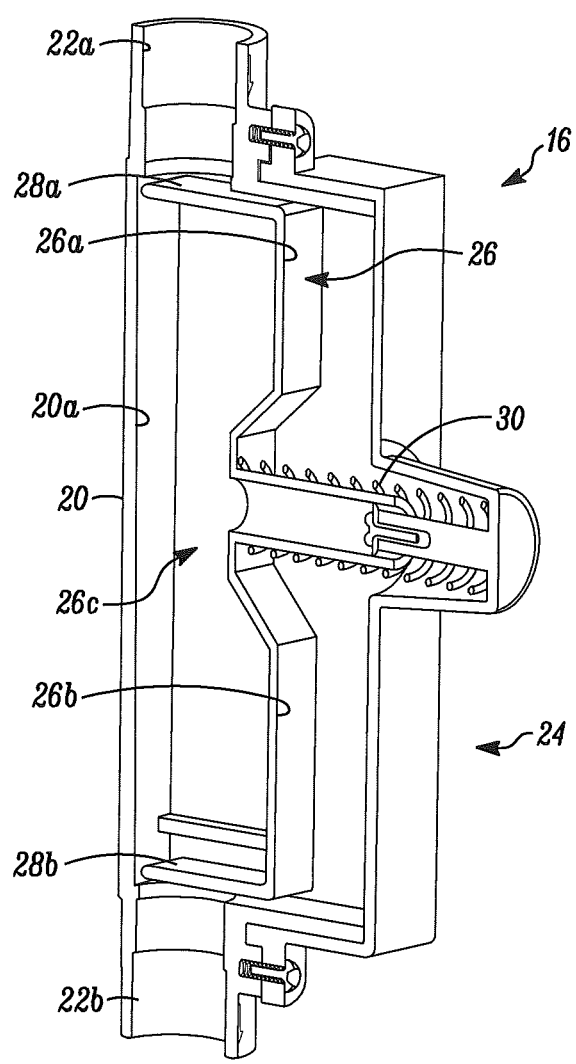
FIG. 2 is a perspective view of the filter in a sectional view.

In FIGS. 1, 2 the pre-filter 16 is in a blocking state wherein fluid flow from inflow port 22a to outflow port 22b is blocked by a biased slider or blocking element 26 carried by cover 24. Element 26 is biased, pushed, via a spring 30 to a flow blocking state4, as illustrated in FIGS. 1, 2. Spring 30 can be carried on cover 24 or on housing 20 without limitation.

Blocking element 26 can include first and second elongated sections 26a, 26b joined by a center section 26c. Section 26c also engages the spring 30 which provides a blocking state force such that one or both of the end regions 28a, 28b (depending if the member 26 has one or two blocking regions) blocks flow into or out of the housing 20 at inlets 22c, 22d. Those of skill will understand that only one blocking end region, such as 28a, 28b is required to block flow through housing 20.

When flow through the housing 20 is interrupted by the blocking member 26 as described above, the drop in velocity of air into detector 18 can be sensed thereby and via circuits 18a. In response to the sensed drop in velocity, a trouble indicator can be generated and sent to a monitoring unit.

Figure 3:
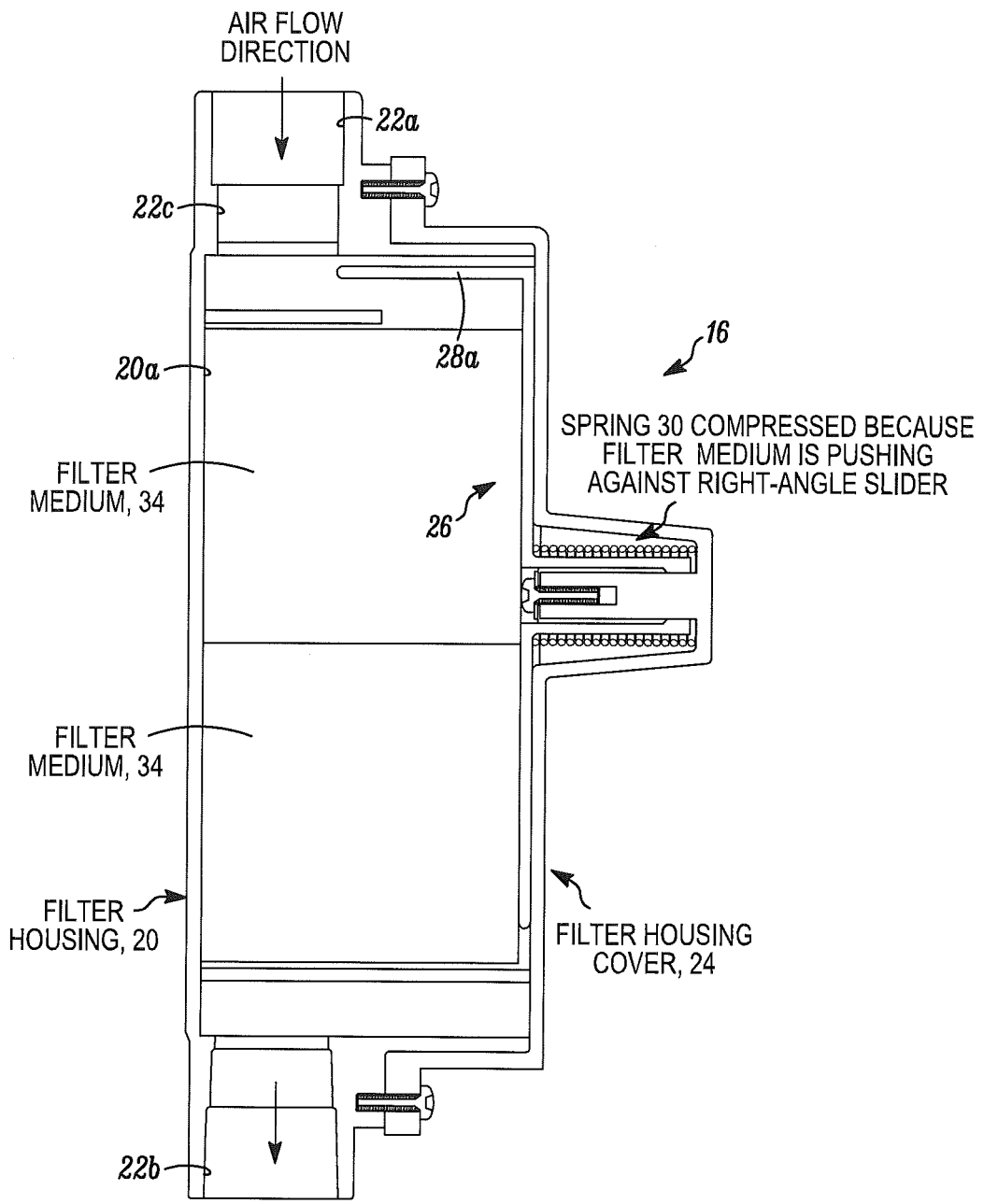
FIG. 3 is a side sectional view of a filter in accordance herewith with the filter element installed.
Figure 4:
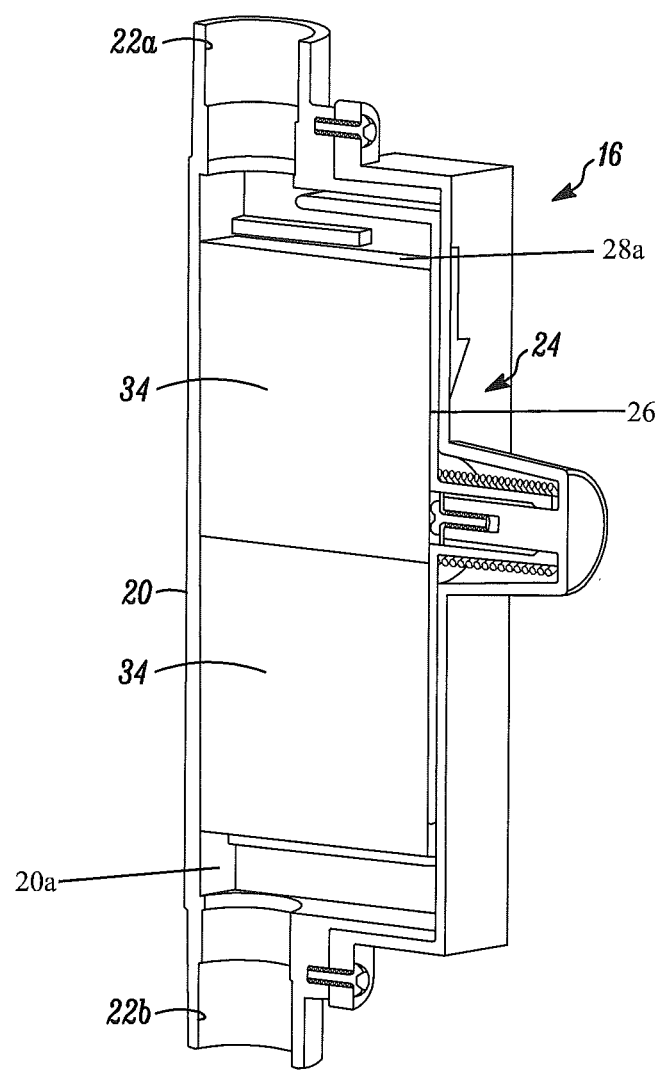
FIG. 4 is a perspective view of the filter in a sectional view with the filter element installed.

FIGS. 3, 4 illustrate pre-filter 16 in a flow state. Elements of pre-filter 16 in FIGS. 3, 4 that are the same as corresponding elements in FIGS. 1, 2 are designated with the same identification numerals and need not be discussed further.

In FIGS. 3, 4 a replaceable filter medium 34 is positioned in the internal region 20a. The slidable blocking element 26 is displaced from the blocking state, of FIGS. 1, 2, to a flow state with spring 30 compressed by the filter medium 34. When element 26 is retracted as illustrated in FIGS. 3, 4 member 28a, and 28b (if present) is, are retracted from blocking inlet 22c, and outlet 22d. As a result, fluid or atmospheric flow is permitted through the pre-filter 16.

If the filter element 34 is removed for replacement, the biasing spring 30 forces the slidable blocking element 26 to reclose the path through housing 20 as explained above relative to FIGS. 1, 2. This reclosure of filter 16 will be detected by aspirated 18 and an indicator can be generated by circuitry 18a.

In summary, pre-filter 16 provides a blocked state when the filter element 34 is removed to prevent pollution from entering the sensing chamber of detector 18. When the filter element 34 is reinserted, pre-filter 16 again exhibits a flow state.

The preferred types of filters, such as 34, along with their filtering characteristics would be understood by those of skill. Those parameters need not be discussed further.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

Further, logic flows depicted in the figures do not require the particular order shown, or sequential order, to achieve desirable results. Other steps may be provided, or steps may be eliminated, from the described flows, and other components may be add to, or removed from the described embodiments.

The invention claimed is:

1. A pre-filter apparatus comprising:
a housing with a fluid flow inflow port and a fluid flow outflow port, the housing defining, in part, an interior region;
a blocking member carried in the interior region and movable relative to the housing; and
a replaceable filter element disposed between the housing and the blocking member,
wherein the blocking member engages a biasing element to provide a blocking force such that, when the replaceable filter element is removed, the blocking member blocks fluid flow into and out of the housing through both the fluid flow inflow port and the fluid flow outflow port.

2. The pre-filter apparatus as in claim 1 further comprising a cover.

3. The pre-filter apparatus as in claim 2 wherein the cover closes the interior region.

4. The pre-filter apparatus as in claim 3 wherein the biasing element includes a spring.

5. The pre-filter apparatus as in claim 1 wherein the replaceable filter element displaces the blocking member by compressing the biasing element to retract the blocking member and allow the fluid flow into and out of the housing through both the fluid flow inflow port and the fluid flow outflow port.

6. The pre-filter apparatus as in claim 5 wherein the biasing element includes a compression spring.

7. The pre-filter apparatus as in claim 1 wherein the blocking member includes a first elongated portion and a second portion, the second portion being shorter than the first elongated portion and oriented on an order of ninety degrees thereto.

8. The pre-filter apparatus as in claim 7 wherein the blocking member carries a third portion displaced from the second portion and parallel thereto.

9. The pre-filter apparatus as in claim 8 wherein the blocking member moves laterally relative to a selected line between the fluid flow inflow port and the fluid flow outflow port.

10. An apparatus comprising:
an aspirated detector; and
a pre-filter having an inflow port and an outflow port,
wherein the outflow port is coupled to the aspirated detector,
wherein the pre-filter carries a removable filter element configured such that, when the removable filter element is removed, fluid flow through the pre-filter is blocked through the inflow port and the outflow port,
wherein the pre-filter includes a spring loaded blocking member in a blocking state when the removable filter element is not present,
wherein the removable filter element, when present, displaces the spring loaded blocking member from the blocking state to a fluid flow state,
wherein the spring loaded blocking member, when in the blocking state, blocks the fluid flow through the inflow port and the outflow port,
wherein the spring loaded blocking member, when in the fluid flow state, allows the fluid flow through the inflow port and the outflow port,
wherein the spring loaded blocking member includes a spring to move the spring loaded blocking member between the blocking state and the fluid flow state,
wherein the pre-filter includes a housing,
wherein the spring loaded blocking member is removably attached to the housing, and
wherein the removable filter element, when present, is disposed between the housing and the spring loaded blocking member.

11. The apparatus as in claim 10 wherein the removable filter element, when present, is positioned in the pre-filter between the inflow port and the outflow port.

12. The apparatus as in claim 10 wherein the aspirated detector emits a trouble indicator when the fluid flow through the pre-filter is blocked.

13. The apparatus as in claim 10 wherein the housing is elongated and the spring loaded blocking member moves laterally from the fluid flow state to the blocking state in response to the spring.

* * * * *